US008858063B1

(12) United States Patent
Agren

(10) Patent No.: US 8,858,063 B1
(45) Date of Patent: Oct. 14, 2014

(54) DILUTION KIT AND METHOD

(75) Inventor: Stuart H. Agren, Mesa, AZ (US)

(73) Assignee: SAPA-IP, LLC, Tempe, AZ (US)

( * ) Notice: Subject to any disclaimer, the term of this patent is extended or adjusted under 35 U.S.C. 154(b) by 715 days.

(21) Appl. No.: 12/418,240

(22) Filed: Apr. 3, 2009

(51) Int. Cl.

| | |
|---|---|
| ***B01F 15/02*** | (2006.01) |
| ***A45C 11/34*** | (2006.01) |
| ***B65D 69/00*** | (2006.01) |
| ***B65D 71/00*** | (2006.01) |
| ***B65D 85/44*** | (2006.01) |
| ***B65D 85/04*** | (2006.01) |
| ***B65D 85/42*** | (2006.01) |
| ***B65D 85/20*** | (2006.01) |
| ***B65D 73/00*** | (2006.01) |
| ***B65D 75/00*** | (2006.01) |
| ***B65D 25/08*** | (2006.01) |
| ***B65D 81/24*** | (2006.01) |
| ***B01L 3/00*** | (2006.01) |
| ***G01N 31/22*** | (2006.01) |
| ***G01N 33/52*** | (2006.01) |
| ***A61M 37/00*** | (2006.01) |
| ***A61M 31/00*** | (2006.01) |

(52) U.S. Cl.
USPC ........... 366/134; 206/214; 206/569; 206/426; 206/538; 206/446; 206/486; 206/134; 206/219; 206/568; 206/443; 206/211; 422/430; 604/518; 604/82

(58) Field of Classification Search
USPC .......... 366/134; 206/219, 568, 443, 214, 569, 206/426, 538, 446, 486, 211; 422/430; 604/82, 518
See application file for complete search history.

(56) References Cited

U.S. PATENT DOCUMENTS

| | | | | | |
|---|---|---|---|---|---|
| 1,986,403 | A * | 1/1935 | Lehmkuhl | 436/125 |
| 3,857,423 | A * | 12/1974 | Ronca, Jr. | 141/5 |
| 5,570,780 | A * | 11/1996 | Miller | 206/305 |
| 6,467,619 | B1 * | 10/2002 | Leen et al. | 206/421 |
| 6,779,566 | B2 * | 8/2004 | Engel | 141/25 |
| 6,779,665 | B2 * | 8/2004 | Bolanos | 206/569 |
| 2006/0145847 | A1 * | 7/2006 | Simpson et al. | 340/568.1 |

FOREIGN PATENT DOCUMENTS

EP 0397607 * 4/1989

* cited by examiner

*Primary Examiner* — Richard Crispino
*Assistant Examiner* — Matthew Hoover
(74) *Attorney, Agent, or Firm* — Jackson White, PC; Steven J. Laureanti

(57) ABSTRACT

A dilution kit for and a method of diluting concentrated solutions used to treat allergic symptoms are disclosed. The dilution kit may comprise a case comprising: a base; and a cover hingedly coupled to the base. A foam pad may be removably coupled within the base, the foam pad defining a plurality of vial apertures. A plurality of vials may be removably positionable within the plurality of vial apertures. The method may comprise: removably positioning at least one of a plurality of vials in an upwardly facing position within at least one of a plurality of apertures defined in a layer of foam padding in a base of a case of a dilution kit; and placing a predetermined amount of one of a diluent, a concentrated solution, and a combination thereof into at least one empty vial of the plurality of vials.

14 Claims, 2 Drawing Sheets

DILUTION KIT AND METHOD

BACKGROUND

1. Technical Field

This document relates to devices and methods for diluting concentrated solutions.

2. Background

Conventionally, dilution of concentrated solutions is generally accomplished by adding concentrated solution to a diluent solution. Conventional methods of dilution vary as to whether the concentrated solution is added to the diluent or the diluent is added to the concentrate. Conventional dilution systems may use a wide variety of containers and extraction equipment to mix and remove the diluent and the concentrate including vials, syringes, beakers, and graduated cylinders.

Conventional dilution systems involving small containers, such as vials, often are challenging to use during the dilution process because the small size of the container makes it prone to tipping over. When the container tips over, at best the effect is merely annoying; however, at worst, the diluted solution being created may spill out and be rendered completely unusable.

SUMMARY

Aspects of this document relate to dilution kits and methods that improve the ease of use of small containers, such as vials. These aspects may comprise, and implementations may include, one or more or all of the components and steps set forth in the appended CLAIMS, which are hereby incorporated by reference.

In one aspect, a dilution kit is disclosed. A dilution kit for and a method of diluting concentrated solutions used to treat allergic symptoms are disclosed. The dilution kit may comprise a case comprising: a base; and a cover hingedly coupled to the base. A foam pad may be removably coupled within the base, the foam pad defining a plurality of vial apertures. A plurality of vials may be removably positionable within the plurality of vial apertures.

Particular implementations may include one or more or all of the following.

The plurality of apertures in the foam padding may be smaller than the plurality of vials. The plurality of apertures may be one of a same size, a different size, and a combination thereof. An o-ring seal may be provided in a groove along a circumferential edge of the base. The cover may comprise at least one latch that allows the cover to removably couple to the base. The base and the cover may each comprise an aligning locking member. The plurality of vials may be inserted in a specified order in the plurality of apertures corresponding to a label marker on the vials left to right and top to bottom.

In another aspect, a method of diluting concentrated solutions used to treat allergic symptoms is disclosed. The method may comprise the steps of: removably positioning at least one of a plurality of vials in an upwardly facing position within at least one of a plurality of apertures defined in a layer of foam padding in a base of a case of a dilution kit; and placing a predetermined amount of one of a diluent, a concentrated solution, and a combination thereof into at least one empty vial of the plurality of vials.

Particular implementations may include one or more or all of the following.

The step of removably positioning at least one of a plurality of vials may comprise rotating a top of the at least one vial upward while a bottom of the at least one vial remains in the at least one aperture.

The step of removably positioning at least one of a plurality of vials may comprise: removably positioning a concentrated solution vial in an upwardly facing position within a corresponding aperture; and removably positioning an empty final vial in an upwardly facing position within a corresponding aperture.

The step of placing a predetermined amount of one of a diluent, a concentrated solution, and a combination thereof into at least one empty vial may comprise: removing a predetermined amount of concentrated solution from the concentrated solution vial and placing the predetermined amount concentrated solution into the empty final vial.

The method may further comprise: removably positioning a diluent vial in an upwardly facing position within a corresponding aperture; removably positioning at least one empty intermediate vial in an upwardly facing position within a corresponding aperture; removably positioning an empty start vial in an upwardly facing position within a corresponding aperture; removing a predetermined amount of diluent from the diluent vial and placing a portion of the predetermined amount of diluent into each of the at least one empty intermediate vial and the empty start vial; removing a predetermined amount of concentrated solution from the final vial and placing the predetermined amount of concentrated solution into the at least one intermediate vial; and removing a predetermined amount of a solution from the at least one intermediate vial and placing the predetermined amount of solution into the start vial.

The method may further comprise: placing the plurality of vials in a specified order left to right and top to bottom in the plurality of apertures corresponding to a label marker on the vials; inserting dropper tips into predetermined vials; nestling the plurality of vials into their corresponding apertures and removably latching a cover of the case to the base; and/or locking the cover to the base to prevent unauthorized access.

The foregoing and other aspects and implementations of dilution kits and related methods may have one or more or all of the following advantages.

Because all of the vials used to make a solution may be held upwardly facing in an aperture in a layer of foam padding during dilution, the potential for spillage and loss of solution is greatly reduced.

Placing completed vials containing diluted solution into a kit allows a patient for example to conveniently carry and transport the kit while treatments are ongoing.

The foregoing and other aspects, features, and advantages will be apparent to those of ordinary skill in the art from the DESCRIPTION and DRAWINGS, and from the CLAIMS.

BRIEF DESCRIPTION OF DRAWINGS

Implementations will hereinafter be described in conjunction with the appended DRAWINGS (which are not necessarily to scale), where like designations denote like elements, and.

DESCRIPTION

This document features dilution kits for and methods of diluting concentrated solutions used, for example, to treat allergic symptoms. There are many features of dilution kits and methods disclosed herein, of which one, a plurality, or all features may be used in any particular implementation.

In the following description, reference is made to the accompanying DRAWINGS which form a part hereof, and which show by way of illustration possible implementations. It is to be understood that other implementations may be utilized, and structural, as well as procedural, changes may be made without departing from the scope of this document. As a matter of convenience, various components will be described using exemplary materials, sizes, shapes, dimensions, and the like. However, this document is not limited to the stated examples and other configurations are possible and within the teachings of the present disclosure.

Accordingly, there are a variety of dilution kit implementations. Notwithstanding, turning to FIGS. 1-3 and for the exemplary purposes of this disclosure, dilution kit 10 is shown.

Figure 1:
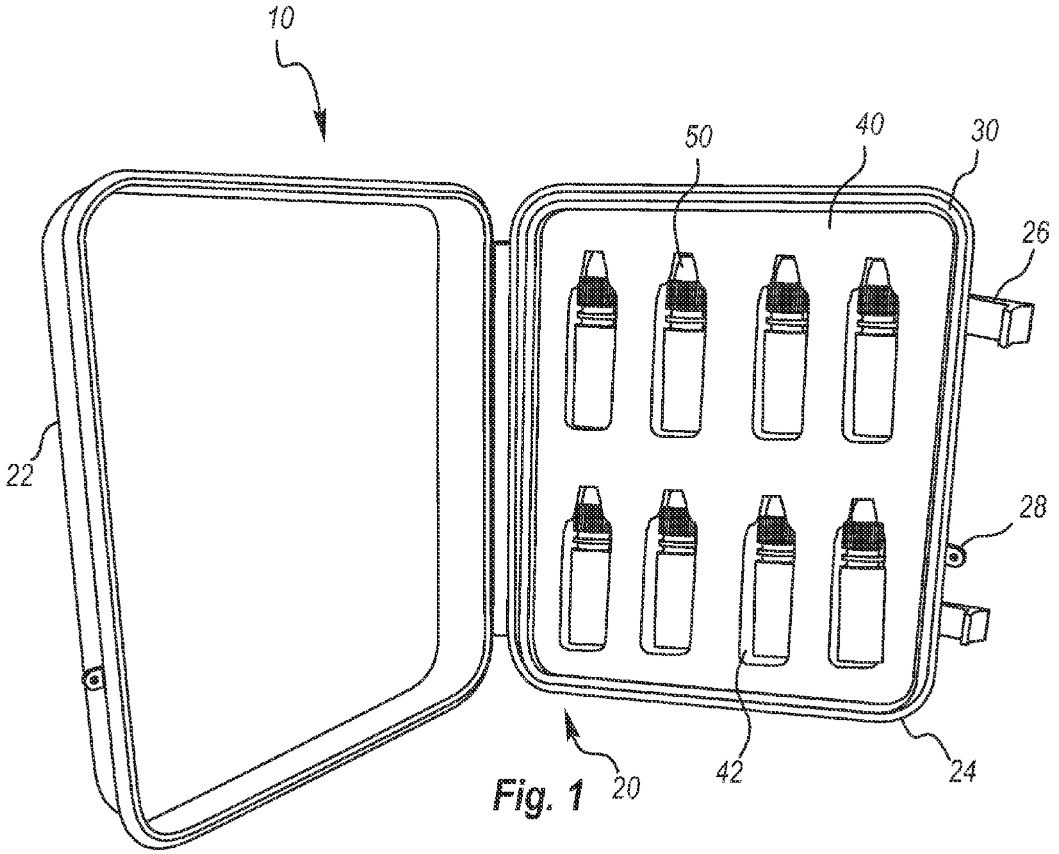
FIG. 1 is a front perspective view of an implementation of a dilution kit.

Referring to FIG. 1, dilution kit 10 is illustrated in an assembled condition. Dilution kit 10 includes a plurality of openings or apertures 42 in foam padding 40 sized to receive a plurality of vials 50. The openings or apertures 42 in foam padding 42 may be slightly smaller than the vials 50. Such a smaller size and the material characteristics of the foam padding itself (e.g., its resiliency, conformity, and the like) maintain the vials with a snug fit not only in a horizontal position entirely within the apertures 42, but in any angular or vertical position with the top of the vials 50 out of the apertures 42 and the bottom of the vials 50 within the apertures 42. Obviously, a different padding could be used that includes similar material characteristics as foam padding.

The foam padding 42 is removably coupled into a base 24 of case or housing 20 which includes an o-ring seal 30 in a groove along its edge. A cover 22 of case or housing 20 is included that is hingedly coupled to base 24 and includes latches 26 that allow cover 22 to latch over base 24. Aligned locking members 28 are included on cover 22 and base 24 and are configured to allow for insertion of a locking device through apertures in locking members 28.

Figure 2:
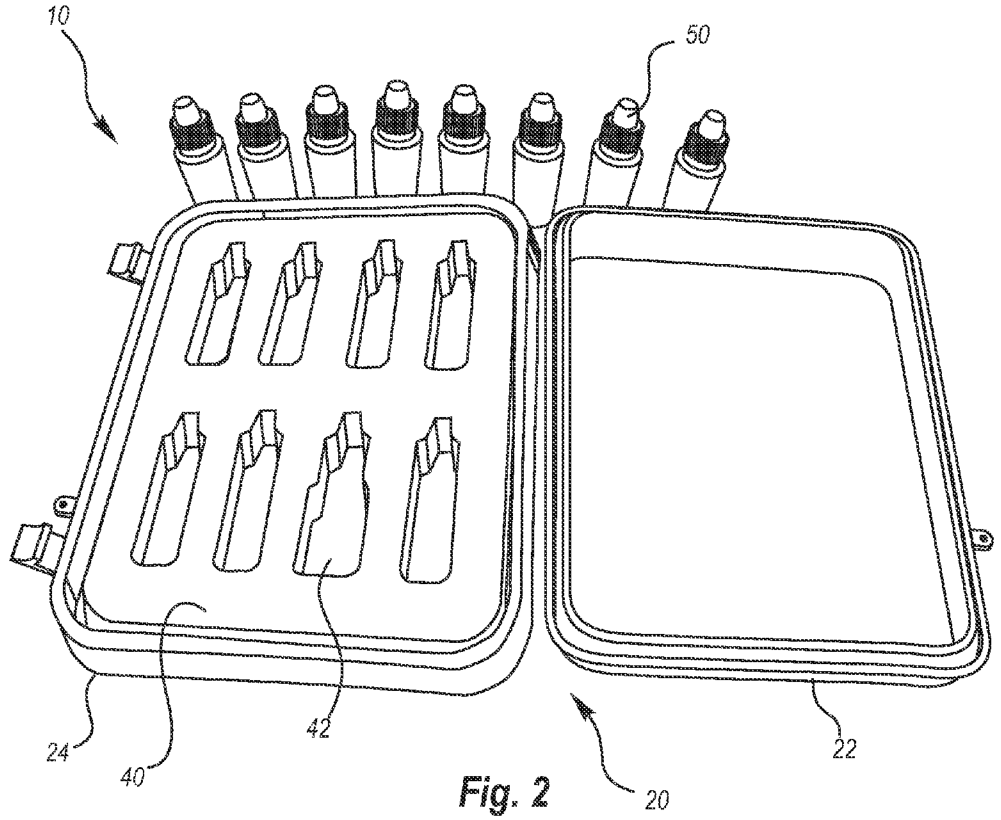
FIGS. 2-3 are top perspective views of the dilution kit implementation illustrated in FIG. 1 during use.

Turning to FIG. 2, dilution kit 10 is illustrated in a disassembled condition. Foam padding 40 could comprise two layers, a top layer having apertures 42 sized to receive each of the vials 50 and a bottom layer (not shown) that fits into base 24 below the top layer. Openings or apertures 42 may be all the same size, all different in size, or contain any combination and/or arrangement of similarly/dissimilarly sized apertures depending in part on the vials 50 used.

Many additional implementations are possible. Further implementations are within the CLAIMS.

It will be understood that dilution kit implementations are not limited to the specific assemblies, devices and components disclosed in this document, as virtually any assemblies, devices and components consistent with the intended operation of a dilution kit implementation may be utilized. Accordingly, for example, although particular assemblies, devices and components are disclosed, such may comprise any shape, size, style, type, model, version, class, measurement, concentration, material, weight, quantity, and/or the like consistent with the intended operation of a dilution kit implementation. Implementations are not limited to uses of any specific assemblies, devices and components; provided that the assemblies, devices and components selected are consistent with the intended operation of a dilution kit implementation.

Implementations of dilution kits and components may be formed of any of many different types of materials or combinations thereof that can readily be formed into shaped objects provided that the materials selected are consistent with the intended operation of a dilution kit implementation. For example, the components may be formed of: rubbers (synthetic and/or natural) and/or other like materials; polymers such as thermoplastics (such as ABS, Fluoropolymers, Polyacetal, Polyamide; Polycarbonate, Polyethylene, Polypropylene (low or high density), Polysulfone, and/or the like), thermosets (such as Epoxy, Phenolic Resin, Polyimide, Polyurethane, Silicone, and/or the like), any combination thereof, and/or other like materials; carbon-fiber, aramid-fiber, any combination thereof, and/or other like materials; composites and/or other like materials; metals; alloys; any other suitable material; and/or any combination of the foregoing thereof.

Various dilution kit implementations may be manufactured using conventional procedures as added to and improved upon through the procedures described here. Some components defining dilution kit implementations may be manufactured simultaneously and integrally joined with one another, while other components may be purchased pre-manufactured or manufactured separately and then assembled with the integral components. Accordingly, manufacture of these components separately or simultaneously may involve vacuum forming, injection molding, blow molding, casting, forging, cold rolling, milling, drilling, reaming, turning, grinding, stamping, pressing, cutting, bending, welding, soldering, hardening, riveting, punching, plating, and/or the like. Components manufactured separately may then be coupled or removably coupled with the other integral components, if necessary, in any manner, such as with adhesive, a weld joint, a solder joint, a fastener (e.g. a bolt and a nut, a screw, a rivet, a pin, and/or the like), washers, retainers, wrapping, wiring, any combination thereof, and/or the like for example, depending on, among other considerations, the particular material forming the components.

Thus, for the exemplary purposes of this disclosure, turning to FIGS. 1 and 2 again, dilution kit 10 may be assembled by placing a layer of foam padding 40 having apertures 42 into the base 24. Optionally, if included, a different layer of foam padding may be placed below foam padding 40. Regardless, then vials 50 may be inserted into apertures 42 in the layer of foam padding 40. In particular implementations, the vials 42 may be inserted in a specified order corresponding to a label marker on the vial. For example, a vial may have a label marker of "#1", and may be placed in the topmost left aperture in the layer of foam padding 40, and the next vial with a label marker of "#2" may be placed in the aperture immediately to the right. This process may be repeated for the remaining vials, moving left to right, top to bottom.

Dilution kit implementations may be used with similar results in a variety of applications. In general and for the exemplary purposes of this disclosure, dilution kit 10 may be used to dilute concentrated solutions through execution of the following steps. An empty vial 52 may be placed in an upwardly facing position within one of the apertures 42 in the layer of foam padding 40 for support during the dilution process. For example, this may be accomplished by rotating the top of the vial 50 upward while the bottom of the vial 50 remains in the aperture 42. Next, the cap of the vial 42 may be removed. Diluent may then be placed into the vial 42, followed by concentrated solution. Because the vial 50 being filled is being held in the upwardly facing position within an aperture 42 in the foam padding 40, it is not free to rotate or fall over. Accordingly, the probability that the vial 42 will overturn and spill its contents is dramatically reduced.

Figure 3:
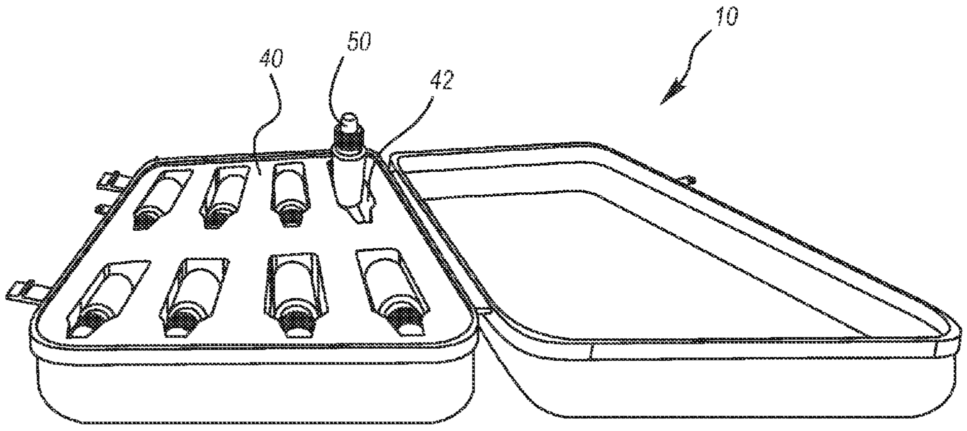

Describing the use of dilution kit implementations further and for the exemplary purposes of this disclosure, dilution kit 10 may be used to dilute serum used to treat allergic symptoms. Turning to FIG. 3, a user (such as a prescribing doctor or even a technician for example) may open the cover 22 of case 20. Any vials 50 present in the apertures 42 in the layer of foam padding 40 may be removed. Alternatively, vials 50 may remain in the apertures 42 in the layer of foam padding 40, and as appropriate, the particular empty vial 52 to be addressed may be placed in an upwardly facing position within its aperture 42 in the layer of foam padding 40 as needed for support during the dilution process (e.g., by rotating to top of the vial 50 upward while the bottom of the vial 50 remains in the aperture 42 as depicted in FIG. 3).

Thus, for the exemplary purposes of this disclosure, a vial 50 labeled "Diluent" for example may be placed in an upwardly facing position in the topmost left hand aperture 42. Next, a user may place a vial 50 (e.g., 50 cc vial) labeled "Start-Up Serum" for example upwardly facing in the aperture immediately to the right of the Diluents vial 50 in the topmost left hand aperture 42. Similarly, a user may place a vial 50 labeled "Final" for example upwardly facing in the aperture immediately to the right of the Serum vial 50. Likewise, a user may place a vial 50 labeled "#2" for example upwardly facing in the aperture immediately to the right of the Final vial 50 (i.e., in FIG. 3, the last aperture 42 in the top row of apertures). Finally, a user may place a vial 50 labeled "#1" for example upwardly facing in the aperture 42 below the #2 vial 50 in the right most aperture 42 in the bottom row of apertures;

Next, a user may take a 10 cc syringe for example and remove 10 cc from the Serum vial 50 and place it into the Final vial 50. Then, with a syringe, a user may remove 8 cc from the Diluent vial 50 and place 4 cc of diluent into both the #2 vial 50 and the #1 vial 50. Next, with a syringe, the user may remove 1 cc of serum from the Final vial 50 and place it into the #2 vial. The #2 vial 50 may then be removed, shaken and then replaced upwardly facing into the aperture 42 from which it came. Then, with a syringe, the user may remove 1 cc of solution from the #2 vial and place it into the #1 vial, upon which the #1 vial may be removed, shaken and then replaced upwardly facing into the aperture 42 from which it came.

Finally, the user may insert dropper tips for example into the appropriate vials. All vials 50 may then be nestled back flat into their corresponding apertures 42 and the cover 22 coupled to base 24 by latches 26. Cover 22 may further be locked to base 24 using locking members 28 and a locking device to prevent unauthorized access.

In places where the description above refers to particular implementations, it should be readily apparent that a number of modifications may be made without departing from the spirit thereof and that these implementations may be alternatively applied. The accompanying CLAIMS are intended to cover such modifications as would fall within the true spirit and scope of the disclosure set forth in this document. The presently disclosed implementations are, therefore, to be considered in all respects as illustrative and not restrictive, the scope of the disclosure being indicated by the appended CLAIMS rather than the foregoing DESCRIPTION. All changes that come within the meaning of and range of equivalency of the CLAIMS are intended to be embraced therein.

The invention claimed is:

1. A method of diluting concentrated solutions used to treat allergic symptoms, the method comprising:
- positioning at least one of a plurality of vials in a reclined position within at least one of a plurality of apertures defined in a layer of foam padding in a base of a case of a dilution kit;
- rotating the at least one of a plurality of vials to an upwardly facing position while a bottom portion of the least one of a plurality of vials remains within the at least one of a plurality of apertures defined in a layer of foam padding in a base of a case of a dilution kit;
- removably positioning an empty final vial in an upwardly facing position within a corresponding aperture;
- removably positioning a diluent vial in an upwardly facing position within a corresponding aperture;
- removably positioning at least one empty intermediate vial in an upwardly facing position within a corresponding aperture;
- removably positioning an empty start vial in an upwardly facing position within a corresponding aperture;
- removing a predetermined amount of concentrated solution from a concentrated solution vial and placing the predetermined amount of concentrated solution from the concentrated solution vial into the empty final vial;
- removing a predetermined amount of diluent from the diluent vial and placing a portion of the predetermined amount of diluent from the diluent vial into each of the at least one empty intermediate vial and the empty start vial;
- removing a predetermined amount of concentrated solution from the final vial and placing the predetermined amount of concentrated solution from the final vial into the at least one intermediate vial; and
- removing a predetermined amount of a solution from the at least one intermediate vial and placing the predetermined amount of solution from the at least one intermediate vial into the start vial.

2. The method of claim 1 further comprising placing the plurality of vials in a specified order left to right and top to bottom in the plurality of apertures corresponding to a label marker on the vials.

3. The method of claim 1 further comprising inserting dropper tips into predetermined vials.

4. The method of claim 1 further comprising nestling the plurality of vials into their corresponding apertures and removably latching a cover of the case to the base.

5. The method of claim 4 further comprising locking the cover to the base to prevent unauthorized access.

6. A method of diluting concentrated solutions used to treat allergic symptoms, the method comprising:
- positioning at least one of a plurality of vials in an upright position within at least one of a plurality of apertures defined in a layer of foam padding in a base of a case of a dilution kit;
- positioning an empty final vial in an upwardly facing position within a corresponding aperture; and
- positioning a diluent vial in an upwardly facing position within a corresponding aperture;
- positioning at least one empty intermediate vial in an upwardly facing position within a corresponding aperture;
- positioning an empty start vial in an upwardly facing position within a corresponding aperture;
- removing a predetermined amount of concentrated solution from a concentrated solution vial and placing the predetermined amount of concentrated solution from the concentrated solution vial into the empty final vial;
- removing a predetermined amount of diluent from the diluent vial and placing a portion of the predetermined amount of diluent from the diluent vial into each of the at least one empty intermediate vial and the empty start vial;
- removing a predetermined amount of concentrated solution from the final vial and placing the predetermined amount of concentrated solution from the final vial into the at least one intermediate vial; and removing a predetermined amount of a solution from the at least one intermediate vial and placing the predetermined amount of solution from the at least one intermediate vial into the start vial.

7. The method of claim 6 further comprising placing the plurality of vials in a specified order left to right and top to bottom in the plurality of apertures corresponding to a label marker on the vials.

8. The method of claim 6 further comprising inserting dropper tips into predetermined vials.

9. The method of claim 6 further comprising nestling the plurality of vials into their corresponding apertures and removably latching a cover of the case to the base.

10. The method of claim 9 further comprising locking the cover to the base to prevent unauthorized access.

11. The method of claim 1, wherein the predetermined amount of concentrated solution from the concentrated solution vial is approximately 10 mL, the predetermined amount of concentrated solution from the final vial is approximately 1 mL, the portion of the predetermined amount of diluent from the diluent vial is approximately 4 mL, and the predetermined amount of the solution from the at least one intermediate vial is 1 mL.

12. The method of claim 6, wherein the predetermined amount of concentrated solution from the concentrated solution vial is approximately 10 mL, the predetermined amount of concentrated solution from the final vial is approximately 1 mL, the portion of the predetermined amount of diluent from the diluent vial is approximately 4 mL, and the predetermined amount of the solution from the at least one intermediate vial is 1 mL.

13. The method of claim 5, wherein the step of locking the cover to the base to prevent unauthorized access comprises placing a locking device through apertures located on locking members coupled to the case.

14. The method of claim 10, wherein the step of locking the cover to the base to prevent unauthorized access comprises placing a locking device through apertures located on locking members coupled to the case.

* * * * *